(12) United States Patent
Snyder et al.

(10) Patent No.: US 7,027,864 B2
(45) Date of Patent: Apr. 11, 2006

(54) DEFIBRILLATION SYSTEM AND METHOD DESIGNED FOR RAPID ATTACHMENT

(75) Inventors: David Snyder, Bainbridge Island, WA (US); Tom Lyster, Bothell, WA (US); Jon Bishay, Woodinville, WA (US); Gust Bardy, Seattle, WA (US); Carl Morgan, Bainbridge Island, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 537 days.

(21) Appl. No.: 10/124,037

(22) Filed: Apr. 17, 2002

(65) Prior Publication Data

US 2003/0199929 A1    Oct. 23, 2003

(51) Int. Cl.
*A61N 1/18* (2006.01)
(52) U.S. Cl. .......................................................... 607/5
(58) Field of Classification Search ............... 607/5, 607/8, 142; 600/508; 601/41; 324/689
See application file for complete search history.

(56) References Cited

U.S. PATENT DOCUMENTS

| 5,197,479 | A  | * | 3/1993 | Hubelbank et al. | 600/508 |
| 5,951,598 | A  | * | 9/1999 | Bishay et al. | 607/142 |
| 6,234,985 | B1 | * | 5/2001 | Lurie et al. | 601/41 |
| 6,241,751 | B1 |   | 6/2001 | Morgan et al. | |
| 6,603,318 | B1 | * | 8/2003 | Hansen et al. | 324/689 |

\* cited by examiner

*Primary Examiner*—George Manuel
(74) *Attorney, Agent, or Firm*—Tony Piotrowski

(57) ABSTRACT

A defibrillator having a pair of electrodes for delivering an impedance-compensated defibrillation shock and a method thereof is provided. The defibrillator can be deployed rapidly and effectively with no or minimal clothing and hair removal. To achieve this, one electrode is coupled to a neck region of the patient, whereas the other electrode is coupled to the patient's body. Both attachment areas are easily accessible to the rescuer, thus allowing a minimally trained user to easily deploy the defibrillator to treat the patient. A wide range of energy levels that are safe for the patient can be generated selectively based on the patient impedance. The presence of voids in the electrodes decrease the effective shock impedance of the electrodes, thus allowing the defibrillator to operate at a lower level of energy when delivering the electrical pulse to the victim's heart.

57 Claims, 7 Drawing Sheets

DEFIBRILLATION SYSTEM AND METHOD DESIGNED FOR RAPID ATTACHMENT

BACKGROUND OF THE INFORMATION

1. Field of the Invention

The present invention relates to equipments used in the electrical treatment and monitoring of human bodies. More specifically, the present invention relates to a defibrillator using impedance-compensated defibrillation pulses to apply treatment by contact with the surface of a patient's skin, which is most conveniently accessible to the rescuer.

2. Description of the Related Art

Sudden cardiac arrest is often caused by ventricular fibrillation (VF) in which abnormal and very fast electrical activity occurs in the heart. During VF, the heart cannot pump blood effectively as it causes the individual muscle fibers within the heart to contract in an unsynchronized way. In treating victims of cardiac arrest with a defibrillator, it is important that the treatment be performed very rapidly as their chances of surviving the cardiac arrest decrease drastically over time following the cardiac arrest. Studies have shown that defibrillation shocks delivered within one minute after VF achieve up to 100% survival rate. However, the survival rate falls to approximately 30% if 6 minutes elapse before the defibrillation shock is delivered. Beyond 12 minutes, the survival rate is almost zero. Therefore, a quick response to cardiac arrest in administering a defibrillation shock at the rescue scene is critical.

Medical equipment manufacturers have developed Automated Electronic Defibrillators (AEDs) to provide early defibrillation. AEDs deliver a high-amplitude current pulse, waveform, or shock to the heart in order to restore the patient's heart rhythm to a normal level. AEDs are widely deployed in both medical and non-medical settings, including private residences, public buildings, public transportation vehicles, airplanes, businesses, etc. AEDs are equipped with a pair of electrodes to deliver a series of shocks to a patient as needed. An electrode may include a conductive foil layer that resides upon a conductive adhesive layer, a lead wire electrically connected to the conductive foil layer to the AED, and an insulation layer for covering the conductive foil layer. The adhesive layer serves to physically and electrically displace the conductive foil layer to a patient's skin. Electrodes tend to deteriorate in time; thus, it is necessary to know their operating condition when they are used in a life-threatening situation. To this end, AEDs rely on a release liner with multiple openings to determine whether the electrodes are in a proper operating condition. When manufacturing electrodes, new electrodes are detachably mounted on a release liner in a package. Prior to use, an impedance is measured through the release layer disposed between a pair of electrodes; if the measurement is higher than the threshold impedance, the electrode is considered to be damaged, deteriorated, unfit for use.

FIG. 1 depicts the conventional AED 10 being applied to a cardiac arrest victim 2 by a rescuer 4. As shown in FIG. 1, a pair of defibrillation electrodes 12 and is placed on anterior-anterior (AA) positions on the victim's torso. The rescuer selects different sizes of electrodes 12 for defibrillating adults and children. A main drawback of the conventional AED 10 is that it requires time-consuming steps in the deployment and use of a defibrillator. First, the placement of electrodes 12 necessitates removing clothes from an unconscious patient 2, sometimes requiring the use of a scissor 8 or knife in order to gain access to the desired location on the torso of the patient 2. Removing clothes causes a longer delay for the patient 2 in waiting for the defibrillating shock. In a highly stressful emergency situation, inexperienced or infrequent operators of the AED 10 are often reluctant or do not aggressively destroy the clothing on an unconscious stranger to expose the recommended attachment areas, and further slow the rescue attempt. In addition, some victims of cardiac arrest require removal of chest hair with a razor 6 to gain access to the attachment areas, which further delays the life-saving shock treatment, thus delaying and reducing the chances of a successful rescue attempt. Moreover, even after gaining access to and attaching the defibrillation electrodes 12 by the trained rescuers of the AED 10, the delivery of the defibrillation shock often fails because the rescuers inadvertently fail to apply the electrode pads correctly, thus missing the heart. The placement of the electrodes is then repeated, which is undesirable in the course of administering the defibrillating shock Accordingly, there is a need for an improved defibrillator that is easy to use and that enables a minimally trained user to easily, rapidly, and effectively deploy the defibrillator to treat the patient, with no or minimal clothing and hair removal.

SUMMARY OF THE INVENTION

The present invention is directed to a method and system for quickly and accurately applying the defibrillating shock to a victim of sudden cardiac arrest.

According to an aspect of the invention, the apparatus may include a pair of electrodes having an opening adapted to make electrical contact with a patient, where one electrode is disposed on a neck region of the patient and the other electrode is disposed on the patient's body; a switch coupled to the pair of electrodes; an energy storage for providing a plurality of energy level outputs across the electrodes to the patient; and, a controller coupled to the switch and the energy storage for determining the need to apply the defibrillation shock to the patient and for determining the desired energy level output based on a patient impedance. The electrodes are coupled to an ECO front end for obtaining the patient impedance. The apparatus may further include a voltage charger coupled to the energy storage for charging a plurality of capacitors therein; a power source for supplying electrical power to the voltage charger; a timer associated with the controller; and, an LCD display. The energy storage may include a plurality of capacitors and a plurality of resistors that are arranged in series or parallel arrangement, or a combination of series and parallel arrangement. The defibrillation shock may be an impedance-compensated defibrillation shock that can be generated by setting the switch according to one of the energy level outputs in response to the patient impedance. Furthermore, the defibrillation shock may comprise one of monophasic, biphasic, and multiphasic. The electrodes according to an embodiment of the present invention may include a conductive adhesive layer and a conductive layer having an opening coupled to the conductive adhesive layer. A release liner, which may include a moisture permeable membrane and a moisture absorbent membrane, is disposed between the electrodes for testing whether the electrodes are operable. The electrode may include a date by which the electrodes should be used. One side of the electrode may further include an image of the human anatomy showing the actual placement of the electrode on the patient.

According to another aspect of the invention, the method for externally delivering an impedance-compensated defibrillation shock to the heart of a patient may include the steps of: charging a defibrillator having a pair of electrodes to a predefined level prior to detecting the need to apply the defibrillation shock to the patient; coupling the first electrode on a neck region of the patient and the second electrode on the patient's body; detecting a patient impedance if there is a need to apply the defibrillation shock; adjusting the energy level of the defibrillator according to predetermined criteria based on the detected patient impedance; and, discharging the energy source across the pair of electrodes to deliver the defibrillation shock to the patient. The placement of the electrodes according to the invention enables the discharge of the defibrillation shock across the electrodes without removing any body hair or clothing from the patient. The duration of the impedance-compensated defibrillation shock is controlled based on the patient impedance.

According to a further aspect of the invention, the method for externally delivering an impedance-compensated defibrillation shock to the heart of a patient without removing body hair or clothing from the patient may include the steps of: providing a pair of electrodes with an opening therein; providing the electrodes to make electrical contact to the patient, where the pair of electrodes is adapted to determine the need to apply the defibrillation shock to the patient; providing a switch coupled to the electrodes; providing an energy storage coupled to the switch capable of supplying a plurality of energy level outputs across the pair of electrodes; providing a controller to select one of the energy level outputs to deliver the impedance-compensated defibrillation shock to the patient based on the patient impedance; and, discharging the impedance-compensated defibrillation shock across the pair of electrodes to the patient. The method may further include monitoring the heart rate of the patient to determine if a subsequent defibrillation shock is needed, and if so, discharging according to one of the voltage level outputs responsive to the patient impedance.

The foregoing and other features and advantages of the invention will be apparent from the following, more detailed description of preferred embodiments as illustrated in the accompanying drawings in which reference characters refer to the same parts throughout the various views. The drawings are not necessarily to scale, the emphasis instead is placed upon illustrating the principles of the invention.

DETAILED DESCRIPTION OF THE DRAWINGS

A more complete understanding of the method and apparatus of the present invention is available by reference to the following detailed description when taken in conjunction with the accompanying drawings wherein.

DETAILED DESCRIPTION OF THE EMBODIMENTS

In the following description, for purposes of explanation rather than limitation, specific details are set forth such as the particular architecture, interfaces, techniques, etc., in order to provide a thorough understanding of the present invention. For purposes of simplicity and clarity, detailed descriptions of well-known devices, circuits, and methods are omitted so as not to obscure the description of the present invention with unnecessary detail.

Now, a description will be made in detail in regards to this invention with reference to the drawings.

Figure 2:
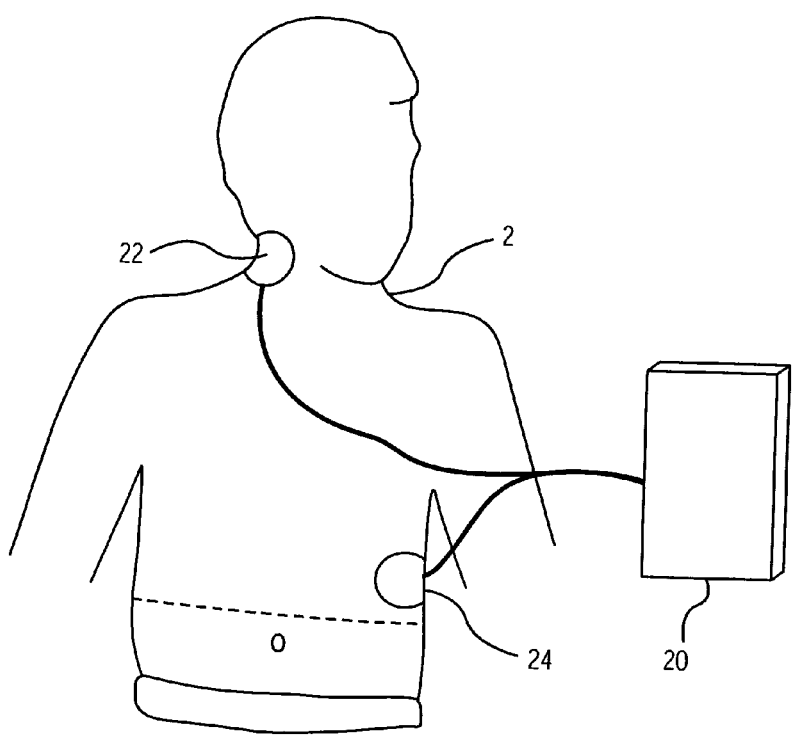
FIG. 2 is an illustration of a defibrillator being applied to a patient under cardiac arrest according to an embodiment of the present invention.

FIG. 2 illustrates a defibrillator system 20 with a pair of electrodes 22 and 24 according a preferred embodiment of the present invention as it would be applied to a cardiac arrest victim 2. As shown in FIG. 2, one electrode 22 (hereinafter referred to as "necktrode") is positioned on the right side of the patient's neck 2, above the collarbone, whereas the other electrode 24 is positioned at the lower left base of the ribs. In particular, the necktrode 22 may be placed on the right side of the patient's neck, such that vertically the top horizontal edge of the necktrode 22 is approximately within 10 cm of the bottom of the patient's right ear lobe and horizontally the centerline of the necktrode 22 is approximately within 10 cm of the vertical midline of the neck when viewing the patient 2 from the side. Although the placement of the necktrode 22 is shown in FIG. 2 for illustrative purposes, it is to be understood that the placement may be lower at the side of the neck, where the neck and shoulder join, or may be positioned in the front of the throat region above the sternal notch or the back of the neck area. The second electrode 24 can be placed quickly by lifting the patient's garment just enough to expose the second attachment area. It is noted that the neck region of the victim 2 below the ear and behind the jaw line as well as the lower left base rib region are conveniently accessible to a rescuer and a relatively hairless area on many individuals, thus requiring no hair or clothing removal to enable the rapid attachment of the electrodes 22 and 24 to the patient's body. Thus, the position of the necktrode 22 in the drawing should not impose limitations on the scope of the invention.

Figure 3:
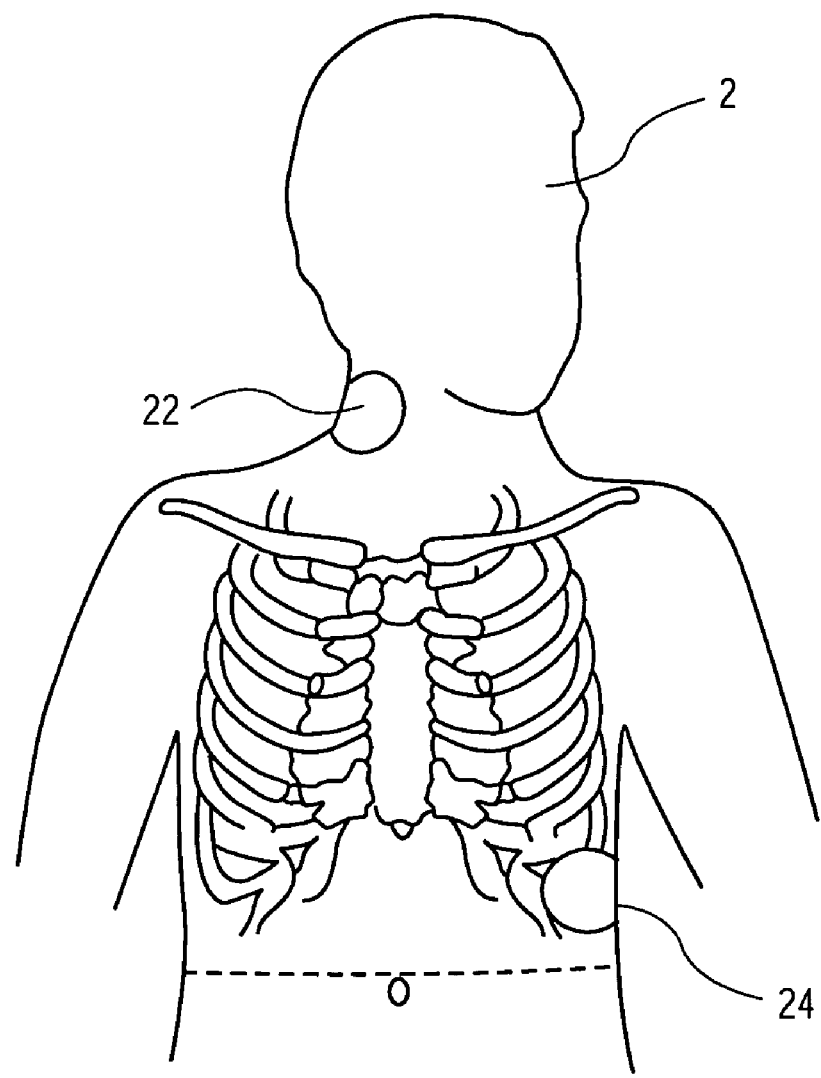
FIG. 3 is a top elevational view of an electrode of the present invention adhered to the patient under cardiac arrest.

Referring to FIG. 3, the provision of delivering a defibrillating shock to a cardiac arrest victim's heart according to the present invention will be explained in a detailed description. In the prior art system, misapplied electrodes can allow the electrical pulse or current to flow along the chest wall, thus missing the victim's heart. As a consequence, the placement of electrodes is repeated, thus delaying the speed with which defibrillation can be performed on the patient. Moreover, experiments have revealed that the electrical waveform delivered by the conventional defibrillators do not flow directly from one electrode to the other electrode. Instead, currents leaving the defibrillator branch out to complex paths, including shunt pathways across the chest surface. Other currents transit the heart through complex routes that are to some degree steered by blood vessel routing and the insulating properties of a surrounding tissue, such as a lung tissue.

In contrast, the present invention provides the placement of the electrodes in specific regions of the victim's body to optimize the defibrillator's effectiveness. As shown in FIG. 3, the electrode placement according to the present invention provides a defibrillation current flow between the necktrode 22 and electrode 24 in order to maximize the efficiency of the placement and to minimize the impedance caused by the chest bones and surrounding tissues. That is, the electrotherapeutic pulses are supplied directly to the victim's heart along the current pathway formed between the necktrode 22 and the electrode 24. The necktrode 22 is placed to gain access to the blood pathway near the neck region (i.e., carotid artery and jugular vein) that leads to the heart. The second electrode 24 is placed over or slightly below the heart's apex on the victim's left chest, on a vertical line below the armpit and horizontally at the approximate bottom of the rib line. This position is easily accessible by pulling up the victim's shirt or other garment on the left side with one hand while positioning the electrode 24 with the other hand. The inventive electrodes 22 and 24 are also substantially small enough to be used in this manner on patients of all ages, including children and adults. On infants, the placement of the electrodes 22 and 24 may shift to the anterior-posterior of the body, such that one electrode is centered on the chest and the other electrode is centered on the back of the infant.

In addition, the present invention renders the placement of the electrodes 22 and 24 for defibrillation without violating the privacy of women as the patient's chest does not have to be completely bared. In the prior art system, the patient's bra has to be removed, especially bras with wires embedded therein, as they interfere with administering the defibrillating shock. These wires impose fewer problems in the present invention as the necktrode 22 is placed so that the wire orientation is relatively normal to the current pathway. Hence, the placement of the electrodes 22 and 24 according to the present invention allows defibrillating a female patient without removing her bra. This in turn eliminates the reluctance of a rescuer when removing a stranger's clothing.

Figure 1:
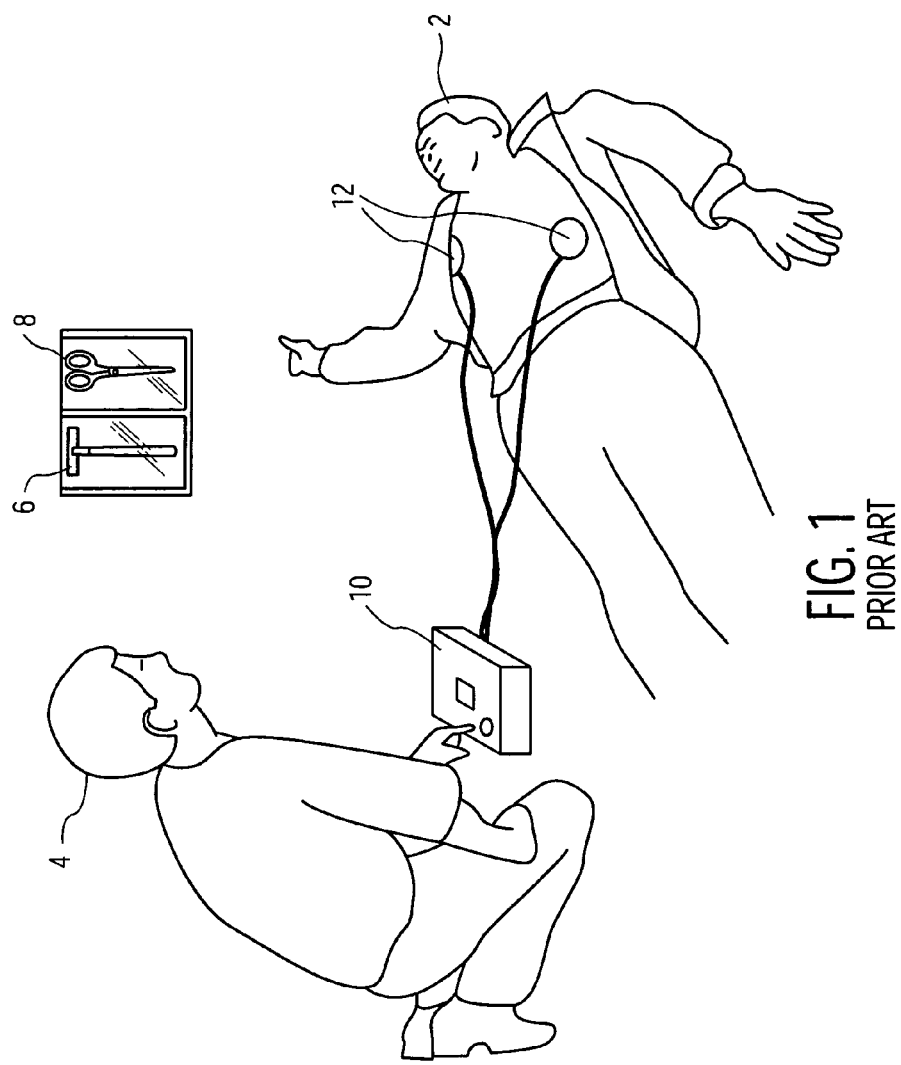
FIG. 1 is an illustration of a conventional defibrillator being applied to a patient under cardiac arrest.
Figure 4:
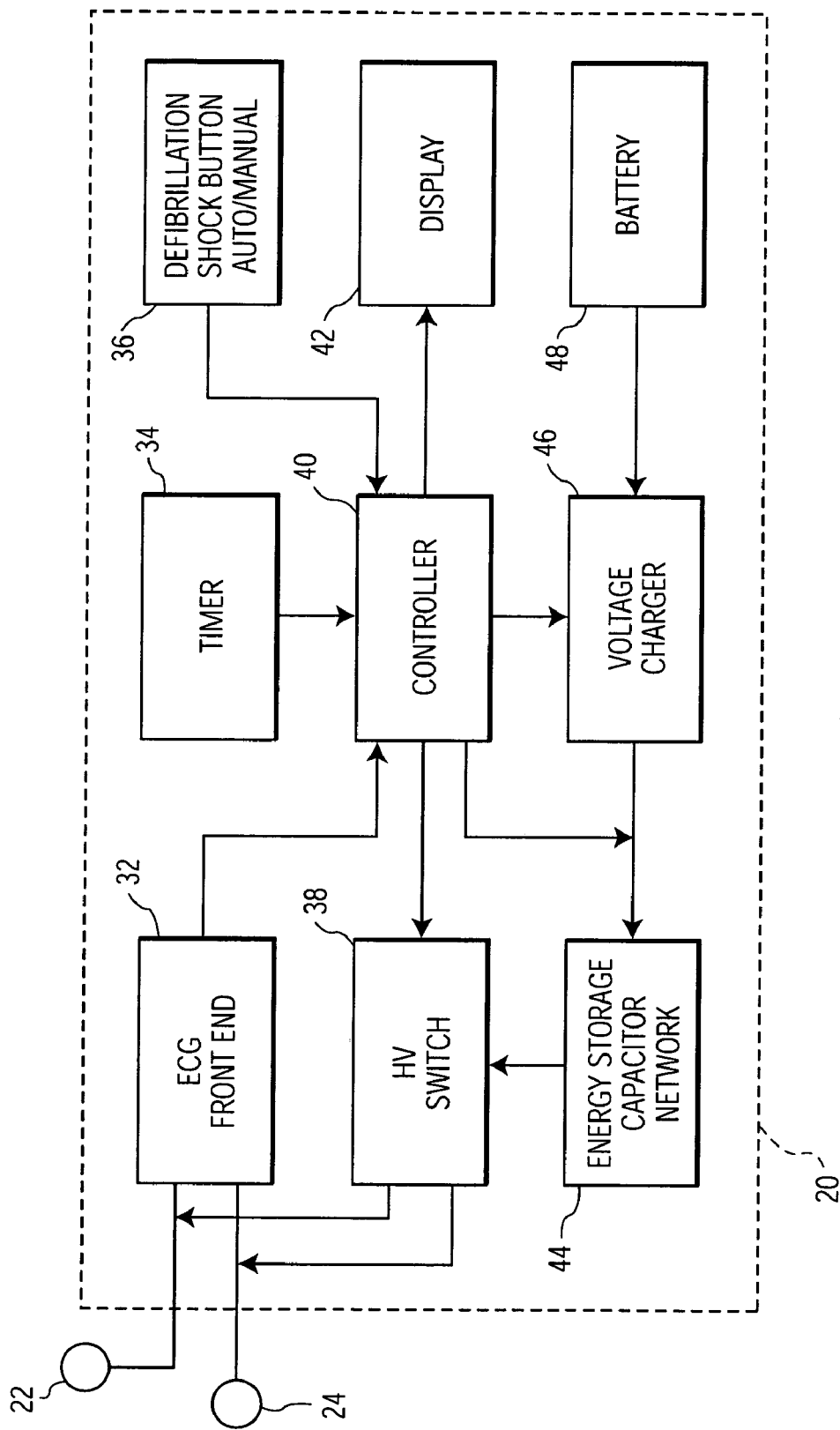
FIG. 4 depicts a representative hardware of the defibrillator 10 illustrated in FIG. 2 according to an embodiment of the present invention.

FIG. 4 is a simplified block diagram of the defibrillator 20 illustrated in FIG. 1 in accordance with the embodiment of the present invention. However, any number of commercially or publicly available defibrillator configured to generate a defibrillation shock can be utilized in various implementations in accordance with the preferred embodiment of the present invention. The defibrillator 20 may include an electrocardiagram (ECG) front end 32, a timer 34, a defibrillation activation button 36, a HV switch 38, a controller 40, a display 42, an energy storage capacitor network 44, a voltage charger 46, and a battery 48. The ECG front end 32 is connected to the electrodes 22 and 24 that are placed on the patient and operates to amplify, filter, and digitize (using an analog to a digital converter) an electrical ECG signal generated by the patient's heart. The detected ECG samples are provided to the controller 40, which runs a shock advisory algorithm for detecting VF or other shockable rhythm requiring treatment by the defibrillation shock. The ECG front end 32 is also capable of measuring the patient impedance across the electrodes 22 and 24 using a low revel test signal that is a non-therapeutic pulse to measure the voltage drop across the electrodes 22 and 24. The detected patient impedance is analyzed by the controller 40 to determine the appropriate energy level desired to be delivered to the patient. As the necktrode 22 is placed directly over major blood vessels close to the contact surface, the ability to sense ECG signals to detect impedance can be improved compared to the prior art The timer 34 is connected to the controller 40 for providing a defibrillation pulse interval or duration when delivering the defibrillation pulse across the electrode pair 22 and 24. The activation button 36 is connected to the controller 40 to enable the user to activate the delivery of a defibrillation pulse across the electrodes 22 and 24 when the VF or other shockable rhythm is detected. The activation button 36 can function in both AED and manual modes in the preferred embodiment. The display 42, connected to the controller 40, is preferably a liquid crystal display (LCD) and provides audio and visible feedback to the user.

The battery 48 provides power for the defibrillator 20 and in particular for the voltage charger 46, which charges the capacitors in the energy storage capacitor network 44. The capacitors in the energy storage capacitor network 44 may be charged to 2300 volts or more. The energy storage capacitor network 44 includes a plurality of capacitors and resistors that are arranged in series or parallel arrangement, or a combination of series and parallel arrangement to supply a plurality of voltage level outputs across the electrodes 22 and 24. It will be apparent to those skilled in the art that a variety of RC arrangements can be implemented to generate different voltage levels. For example, a series resistance of approximately 20 ohms may be inserted in series to deliver electrical power from the battery 48 to the patient. For very high impedance patients, this resistor is shorted during discharge in order to deliver high currents for effective defibrillation. Using lower total delivered energies enables the present system to operate safely for adults and children without requiring the operator to differentiate between the two. Therefore, by selecting an appropriate energy level according to the patient-impedance and the desired energy level determined by the controller 44, a wider range of energy levels can be generated from low to high, without exceeding the maximum threshold value that may be harmful to the patient.

Additional parallel capacitors and resistors may be added as needed to the energy storage capacitor network 44 to increase the total delivered energy of the waveform to the patient. It should be noted that various hardware configurations readily apparent to those skilled in the art can be used for the energy storage capacitor network 44. Alternatively, the function of the energy storage capacitor network 44 can be performed by functionally equivalent circuits, such as a digital processor circuit or an application-specific integrated circuit (ASIC).

The energy storage capacitor network 44 is connected to the HV switch 38. Under the control of the controller 40, the HV switch 38 is configured to sequentially deliver the defibrillation pulse across the pair of electrodes 22 and 24 to the patient in the desired polarity and duration. It should be noted that the HV switch 38 could be adapted to deliver a single polarity (monophasic), both negative and positive polarities (biphasic) or multiple negative and positive polarities (multiphasic) in the preferred embodiment.

In operation, the controller 40 uses the information received from the ECG front end 32 and/or the timer 34 to control the shape of the waveform of the defibrillation pulse delivered to the patient in real time. That is, the total delivered energy of the waveform can be controlled by selecting an appropriate pulse parameter in response to the information received from the ECG front end 32. Here, the defibrillation pulse delivered to the patient may be a fixed level, or a number of defibrillation pulses at different energy levels. This can be achieved by selecting the appropriate voltage level of the energy storage capacitor network 44 from the set of configurations to deliver the desired impedance-compensated defibrillation pulse to the patient. To achieve this, the controller 40 sends a voltage control signal to adjust the charge voltage on each capacitor in the energy storage capacitor network 44 for a subsequent discharge. After each discharge, the patient's heart is monitored simultaneously using the ECG front end 32 to determine if more defibrillation pulses are needed. If so, another set of defibrillation shocks is administered to the patient.

Figure 5A:
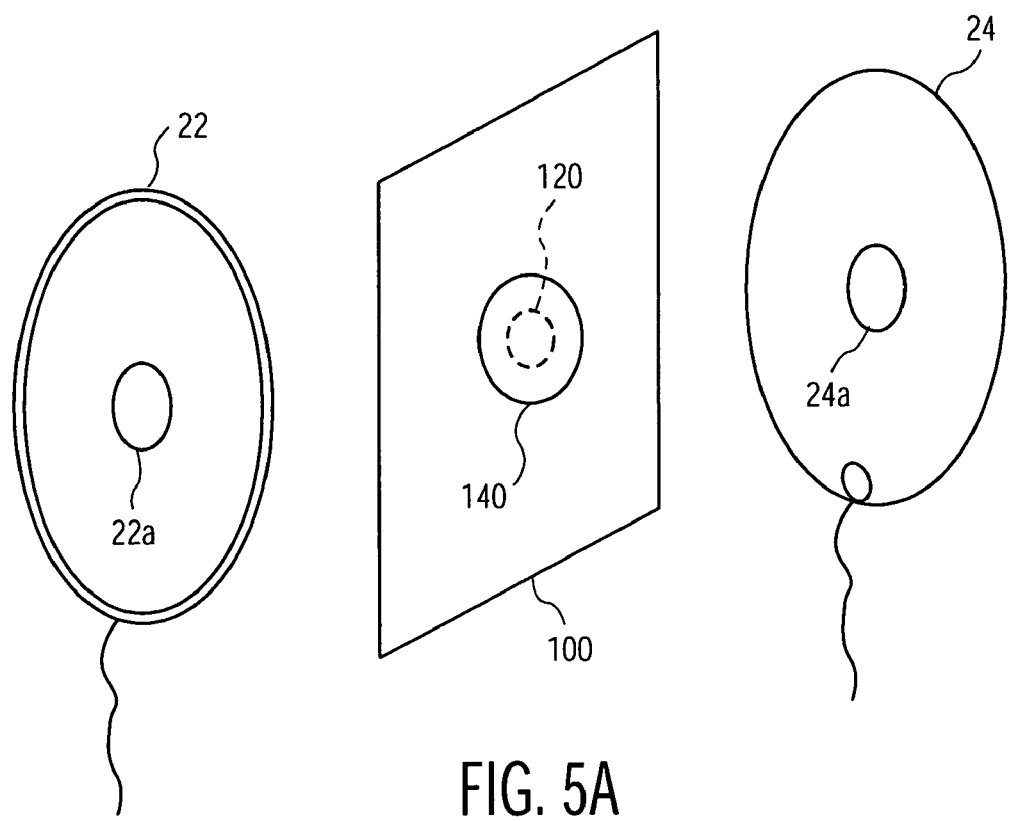
FIG. 5(a) is a perspective view of electrodes mounted upon the release liner according to an embodiment of the present invention.
Figure 5B:
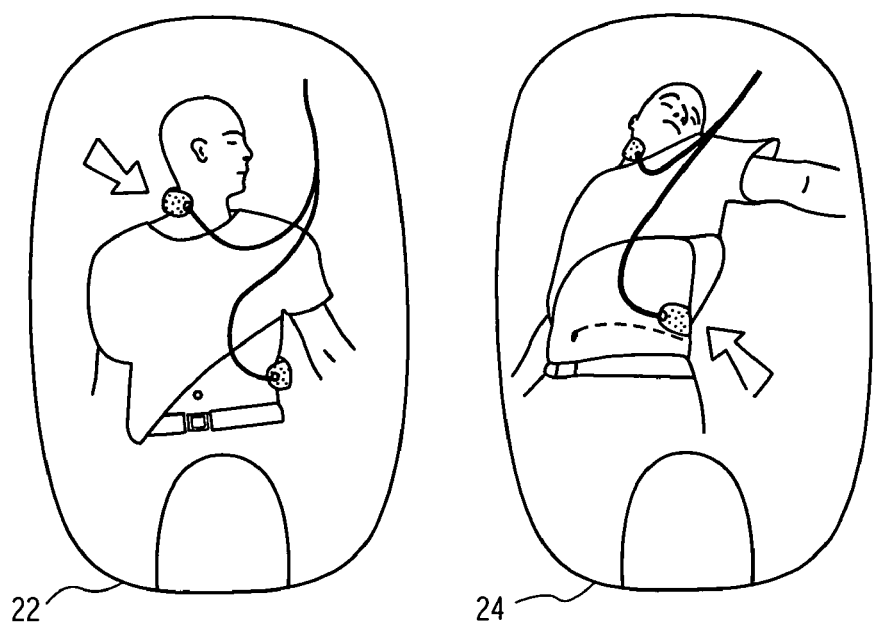
FIG. 5(b) depicts the actual site of electrode placement on one side of the electrode to facilitate installation according to an embodiment of the present invention.

FIG. 5(*a*) is a perspective view of a release liner 100 and a pair of electrodes 22 and 24 according to an embodiment of the present invention. The electrodes and release liner operating in accordance with the present invention may include various embodiments of medically packaged electrodes described in U.S. patent Ser. No. 09/954,750, filed on Sep. 14, 2001, entitled "Medical Electrode and Release Liner Configurations Facilitating Packaged Electrode Characterization," assigned to the same assignee, the teachings of which are incorporated herein by reference.

Figure 6:
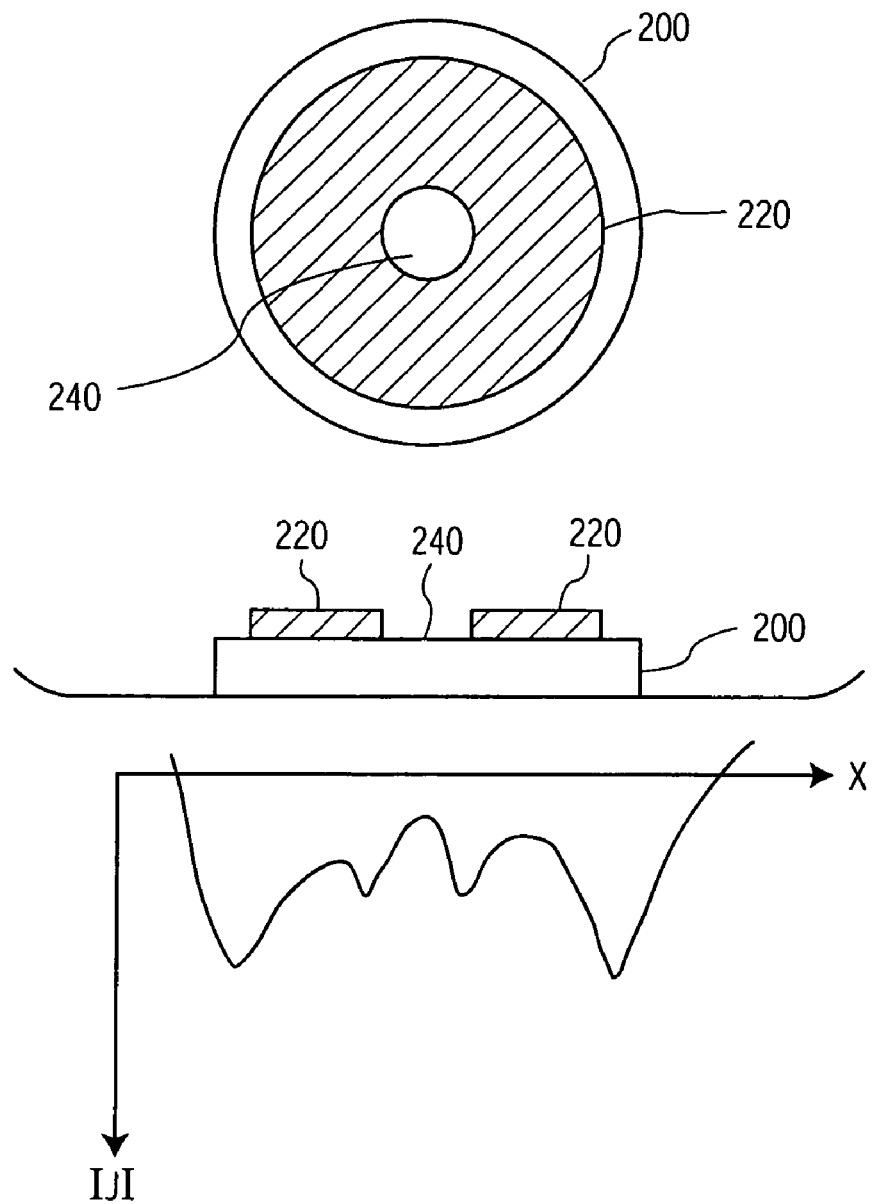
FIG. 6 is a diagram of the electrodes according to an embodiment of the present invention; and, FIG. 7 is a flow chart illustrating the operation steps of the defibrillation system 10 in accordance with the present invention.

Briefly, the release layer 100 may comprise silicon-coated paper, polyester, polypropylene, polyethylene, and/or other non-stick materials, in a manner well understood by those skilled in the art. The opening 120 of the release layer 100 may be cut, stamped, or punched out using conventional techniques, so it can be performed in a variety of ways. The release layer 100 may further include a nonconductive, moisture-permeable and/or moisture-absorbent membrane 140. The electrodes 22 and 24 having at least one opening 22*a* and 24*a*, respectively, may comprise a conductive foil layer that resides in a conductive adhesive layer. The conductive adhesive layer may include a conductive gel layer, such as a hydrogel layer, or other layer having electrical properties. One electrode 22 may be place or positioned upon the release layer 100 so that the electrode's hydrogel layer covers the release layer's opening 120. Similarly, the other electrode 24 may be place or positioned upon the release layer. The placement of the electrodes 22 and 24 upon the release layer allows the electrodes' hydrogel layers to contact the moisture-permeable membrane 140 via the release layer's opening 120. When the electrodes 22 and 24 have been mounted upon the release liner 100, the defibrillator 20 may test the electrical path between the electrodes 22 and 24 by measuring the impedance level. If the measured impedance level is greater than a predefined threshold or range, the defibrillator 20 will indicate that the electrodes 22 and 24 may be unfit for use. The electrodes 22 and 24 may also be handheld paddle electrodes that are used with a manual defibrillator. The total surface of the electrodes is approximately 70 square centimeters for the necktrode 22 and 80 square centimeter for the other electrode 24, meaning that a circular electrode 22 as shown in FIGS. 2, 3, and 6 will have a diameter of about 9.4 cm. A necktrode electrode device of this diameter will only extend a short distance about the neck of a typical adult patient and preferably around less than half the circumference of the neck as shown in these drawings. However, it should be noted that another size of electrodes from the one shown can be used successfully in accordance with the techniques of the present invention. The electrodes 22 and 24 may further include an insulating cover layer and a lead wire that facilitates coupling to the defibrillator 10.

It should be noted that packaged electrodes according to the present invention may include a wrapper, covering, label, or the like that includes an expiration date by which electrodes must be used. An illustrative drawing showing the actual site of electrode placement also may be included on one side of the electrode to facilitate installation, as shown in FIG. 5(*b*).

FIG. 6 is a graph illustrating the electric current density of the electrode 22 and 24 of FIG. 5 when the electrodes 22 and 24 are mounted upon a patient's body. Those skilled in the art will understand that the current flows more easily between an electrode and a patient's body near the electrode's edges. Thus, the current density increases and peaks at the outer edge or border of the electrode's foil layer. However, in the embodiment, the presence of an opening or void 240 in the electrode's foil layer 220 affects the electrical current flowing through or within the electrode. The void 240 may comprise a circular, elliptical, or other shaped opening that is generally disposed within a central region of the foil layer 220. As shown in FIG. 6, the current density drops to a minimum value in the region defined by the void 240, and an additional boundary at which a current density peak occurs in the presence of a void 240. As a result, the presence of one or more voids in the foil layer 220 may decrease the effective shock impedance of the electrodes 22 and 24. Therefore, the defibrillator 20 in accordance with the present invention can operate at a lower level of energy to deliver the electrical pulse to the victim's heart from the surface of the skin.

Figure 7:
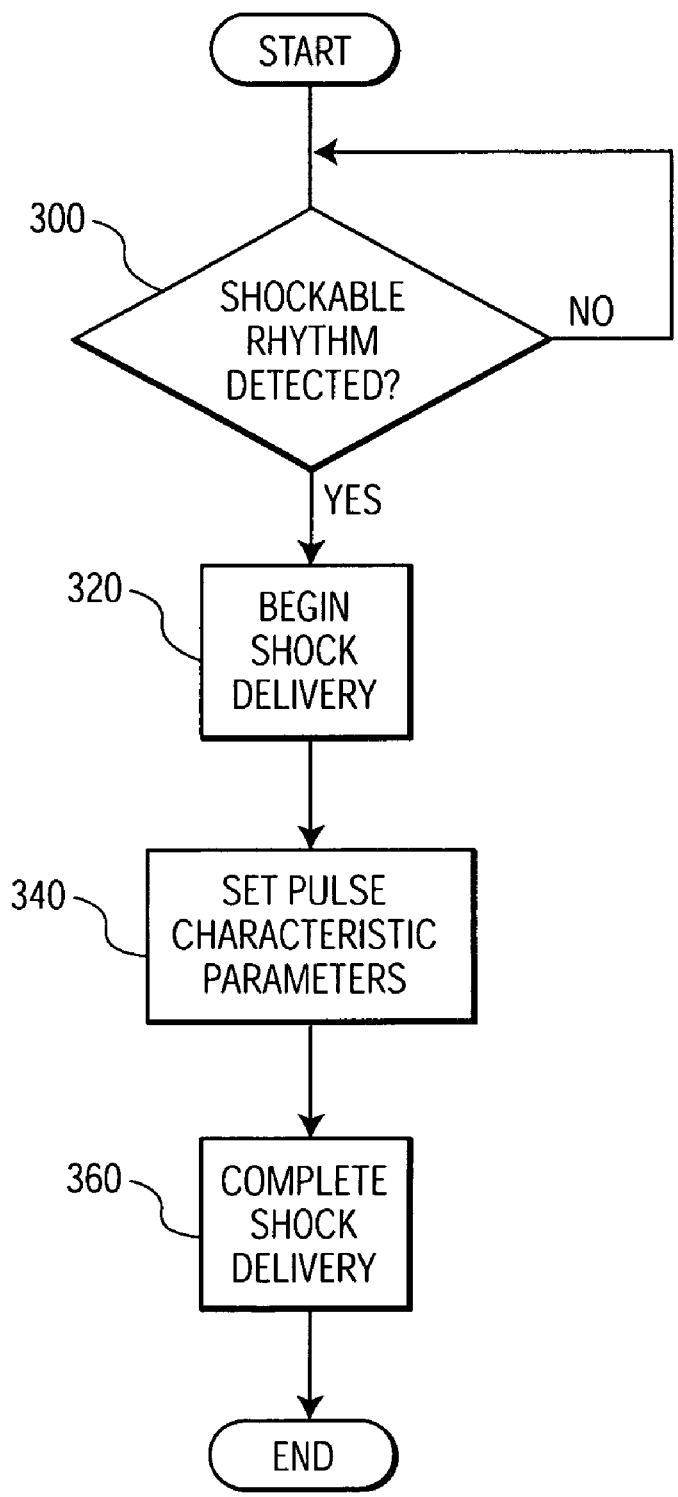

FIG. 7 is a flow chart illustrating the operation steps of delivering an impedance-compensated defibrillation shock according to the present invention. Initially, a test is performed to determine whether the electrodes 22 and 24 are operative by sending an impedance between the electrodes 22 and 24 through the release liner. If the electrodes 22 and 24 are not damaged, the user can then peel off from the adhesive layer and place on the patient's skin as shown in FIG. 3. At the same time, the voltage charger 46 of the defibrillator 20 operates to charge each capacitor of the energy storage capacitor network 44 to a predetermined percentage of the voltage level in order to deliver a defibrillation shock. Thereafter, in step 300, the ECG front end 32 detects a shockable rhythm, i.e., ventricular fibrillation (VF). If no shockable rhythm is detected, the defibrillator 20 continues to detect the ECG information. If a shockable rhythm is detected, the patient impedance is measured by measuring a low-level test signal or delivering a non-therapeutic signal in step 320. The detected shockable rhythm is forwarded to the controller 40 of the defibrillator 20, then the energy level of the defibrillation shock, which may include a series of successive defibrillation shocks at a predetermined interval, to be delivered to the patient is determined. The energy level may be determined by the operator manually, or it can be determined by automatically utilizing a common protocol known in the art.

In step 340, the patient impedance is considered by the controller 40 to select the appropriate energy level output from the set of configurations in the energy storage capacitor network 44. For example, it may be desirable to deliver a higher energy level to a high patient impedance and a lower energy level to a low patient impedance. Here, the controller 40 also determines the polarity and duration of the defibrillation shock. After determining the desired energy level output, the controller 40 sends a signal to the energy storage capacitor network 44 to implement the desired configuration to discharge the desired energy level of defibrillation shock. Thereafter, the controller 40 sends a signal to the HV switch 38 to actuate the switches to discharge the desired defibrillation shock to the patient in step 360. Alternatively, the controller 40 may notify the operator via the display 42 to press the shock button 36 to actuate manually the delivery of the defibrillation shock to the patient. After the discharge of defibrillation shock, the patient's heart is monitored to determine whether a subsequent defibrillation shock is necessary. If so, the above steps may be repeated to deliver the subsequent defibrillation shock.

Having thus described the preferred embodiment of a system and method for delivering an electric pulse, waveform, or shock to the patient's heart, it should be apparent to those skilled in the art that certain advantages have been achieved. In particular, the present invention saves the time previously needed to struggle with clothing removal, thus improving survival odds. The attachment areas in accordance with the present invention minimize the effects of excessive body hair, which prevents effective electrode contact with the patient's skin by eliminating the need to shave a patient's chest prior to the attachment of electrodes. The inventive electrodes are smaller in size and thus easier to store, deploy, and attach to both children and adults. As a result, the same defibrillation protocol may be used on children or adults. The smaller electrode also enables additional miniaturization of the entire defibrillation system. Also, the present invention overcomes or minimizes a rescuer's reluctance in removing clothing from unconscious patients, especially from female patients in fear of violating their privacy.

Furthermore, the inventive system reduces the artifact in the ECG signal caused by movement due to the cardio pulmonary resuscitation (CPR) operation. During the rescue attempt, electrodes are used to gather ECG signals for analysis from the patient's heart. When a rescuer performs chest compressions as part of doing CPR on the patient, the resulting chest movement tends to disturb the electrodes placed on the chest area in the prior art system. This is undesirable as the movement of the electrodes on the chest skin area generates interfering electrical noise or artifacts, which corrupts the ECG signal. Therefore, the placement of the electrodes according to the embodiment of the present invention minimizes such artifact and thus enhances the analysis of the ECG signal during a CPR operation. The ability to analyze the ECO more accurately during a CPR operation reduces the time that CPR must be interrupted during the resuscitation, thereby increasing the chances of a successful rescue attempt.

While the preferred embodiments of the present invention have been illustrated and described, it will be understood by those skilled in the art that various changes and modifications may be made, and equivalents may be substituted for elements thereof without departing from the true scope of the present invention. In addition, many modifications may be made to adapt to a particular situation and the teaching of the present invention without departing from the central scope. Therefore, it is intended that the present invention not be limited to the particular embodiment disclosed as the best mode contemplated for carrying out the present invention, but that the present invention include all embodiments falling within the scope of the appended claims.

What is claimed is:

1. An apparatus for delivering a defibrillation shock to a patient, comprising:
   a pair of electrode devices adapted to make electrical contact with said patient, wherein one electrode device is adapted to be disposed on a neck region of said patient and to extend circumferentially to first and second ends which span an arc which is less than halfway around the circumference of the patient's neck and the other electrode device is adapted to be disposed on the opposite side of said patient's body in the vicinity of the ribcage;
   a switch coupled to said pair of electrode devices;
   an energy storage device for providing a plurality of energy level outputs across said electrodes to said patient; and,
   a controller coupled to said switch and said energy storage device for determining a need to apply said defibrillation shock to said patient and for determining a desired energy level output based on a patient impedance.

2. The apparatus of claim 1, wherein said energy storage device further comprises a plurality of capacitors and a plurality of resistors that are arranged in series, parallel or a combination of series and parallel arrangement.

3. The apparatus of claim 1, further device comprising a voltage charger coupled to said energy storage for charging a plurality of capacitors therein.

4. The apparatus of claim 3, further comprising a power source for supplying electrical power to said voltage charger.

5. The apparatus of claim 1, further comprising an ECG front end coupled to said pair of electrode devicess to determine said patient impedance.

6. The apparatus of claim 1, further comprising an LCD display.

7. The apparatus of claim 1, further comprising a timer associated with said controller.

8. The apparatus of claim 1, wherein said defibrillation shock comprises an impedance-compensated defibrillation shock by setting said switch according to one of said energy level outputs responsive to said desired energy level output.

9. The apparatus of claim 1, wherein said defibrillation shock comprises one of monophasic, biphasic, and multiphasic.

10. The apparatus of claim 1, wherein said electrode devices comprise defibrillation electrodes.

11. The apparatus of claim 1, wherein said controller is coupled to said switch to control the duration and polarity of said defibrillation shock.

12. The apparatus of claim 1, wherein said desired energy level is selected manually by a user.

13. The apparatus of claim 1, wherein the maximum energy level of said defibrillation shock is not harmful to said patient.

14. The apparatus of claim 1, wherein said pair of electrode devices comprising:
   a conductive adhesive layer; and,
   a conductive layer having an opening coupled to said conductive adhesive layer.

15. The apparatus of claim 14, further comprising a release layer disposed between said pair of electrode devices in electrical contact for testing whether said pair of electrode devices is operative.

16. The apparatus of claim 15, wherein said release layer comprises one of a moisture permeable membrane and a moisture absorbent membrane.

17. The apparatus of claim 1, wherein said pair of electrode devices includes a date by which said pair of electrodes should be coupled to said patient.

18. The apparatus of claim 1, wherein one side of said electrode devices includes an image of human anatomy showing the actual placement of said electrode devices on said patient.

19. The apparatus of claim 1, wherein said pair of electrode devices is placed on said patient to deliver said defibrillation shock without removing any clothing from said patient.

20. The apparatus of claim 1, wherein said energy storage device is configured to deliver sequentially said defibrillation shock at said desired energy level output to said patient.

21. The apparatus of claim 1, wherein said pair of electrode devices is placed on said patient to deliver said defibrillation shock without removing body hair from said patient.

22. A system for sequentially delivering an impedance-compensated defibrillation shock to a patient, comprising:
   a first electrode device for coupling to the neck region circumferentially to first and second ends which span an arc which is less than halfway around the circumference of the neck and a second electrode device for coupling to the opposite side of the body of said patient to deliver said defibrillation shock;
   a detector for receiving an ECG signal from said patient;
   a plurality of switches coupled to said first and second electrode devices for selectively directing electrical energy to said patient in one of two polarities;
   a controller for determining a patient impedance based on said ECG signal received from said detector and for selecting a desired energy level based on said patient impedance; and,
   an energy storage device capable of discharging a plurality of energy level outputs, said energy storage is configured to deliver said desired energy level by setting said plurality of switches according to one of said energy level outputs.

23. The system of claim 22, wherein a hole is defined in said first and second electrode devices.

24. The system of claim 22, wherein said energy storage device further comprises a plurality of capacitors and a plurality of resistors that are arranged in series, parallel, or a combination of series and parallel arrangement.

25. The system of claim 24, wherein said first and second electrode devices are placed on said patient to deliver said defibrillation shock without removing any clothing from said patient.

26. The system of claim 22, further comprising a voltage charger coupled to said energy storage device for charging a plurality of capacitors therein.

27. The system of claim 26, further comprising a battery for supplying electrical power to said voltage charger.

28. The system of claim 22, wherein said impedance-compensated defibrillation shock comprises one of monophasic, biphasic, and multiphasic.

29. The system of claim 22, wherein said electrode devices comprise defibrillation electrodes.

30. The system of claim 22, wherein said controller is coupled to said switches to control the duration and polarity of said impedance-compensated defibrillation shock.

31. The system of claim 22, wherein the maximum voltage level of said impedance-compensated defibrillation shock is less than a predetermined threshold value.

32. The system of claim 22, further comprising a release layer disposed between said first and second electrode devices in electrical contact for testing whether said first and second electrode devices are operative.

33. The system of claim 32, wherein said release layer comprises one of a moisture permeable membrane and a moisture absorbent membrane.

34. The system of claim 22, wherein said first and second electrode devices include a date by which said pair of electrodes should be used.

35. The system of claim 22, wherein one side of said first and second electrode devices includes an image of human anatomy showing the actual placement of one of said first and second electrodes on said patient.

36. The system of claim 22, wherein said energy storage device is configured to deliver sequentially said defibrillation shock at said desired energy level output to said patient.

37. The system of claim 22, further comprising a timer associated with said controller.

38. The system of claim 22, further comprising an LCD display.

39. The system of claim 22, wherein said first and second electrode devices are placed on said patient to deliver said defibrillation shock without removing any body hair from said patient.

40. A method for externally delivering an impedance-compensated defibrillation shock to the heart of a patient, the method comprising the steps of:
   (a) charging an energy source of a defibrillator having a pair of electrode devices to a predefined level prior to detecting a need to apply said defibrillation shock to said patient;
   (b) coupling said first electrode device on a neck region of said patient with opposite ends of the device extending less than halfway around the circumference of the neck and said second electrode device on the opposite half of said patient's body in the vicinity of the ribcage;
   (c) detecting a patient impedance if there is a need to apply said defibrillation shock;
   (d) adjusting the energy level of said defibrillator according to predetermined criteria based on said detected patient impedance; and,
   (e) discharging the energy source across said pairs of electrode devices to deliver said defibrillation shock to said patient.

41. The method of claim 40, wherein the duration of said impedance-compensated defibrillation shock is controlled based on said patient impedance.

42. The method of claim 40, wherein said impedance-compensated defibrillation shock comprises one of monophasic, biphasic, and multiphasic.

43. The method of claim 40, wherein said discharging step is performed without removing body hair from said patient.

44. The method of claim 40, further comprising the step of monitoring the heart rate of said patient to determine the need to supply a subsequent defibrillation shock during said discharging step.

45. The method of claim 40, wherein the coupling of said first electrode device and said second electrode device on said patient's body is performed without removing any clothing from said patient.

46. The method of claim 40, wherein the coupling of said first electrode device and said second electrode device on said patient's body is performed without removing any body hair from said patient.

47. The method of claim 46, wherein, if the subsequent defibrillation shock is needed, repeating said steps (d) and (e).

48. The method of claim 40, further comprising the step of performing a cardio pulmonary resuscitation (CPR) on said patient.

49. A method for externally delivering an impedance-compensated defibrillation shock to the heart of a patient, the method comprising the steps of:
   providing a pair of electrode devices adapted to make electrical contact to less than half the circumference of the neck region and to the other half of the body of said patient in the vicinity of the ribcage, said pair of electrode devices adapted to determine a need to apply said defibrillation shock to said patient;
   providing a switch coupled to said electrode devices;
   providing an energy storage device coupled to said switch capable of supplying a plurality of energy level outputs across said pair of electrode devices;

providing a controller to select one of said energy level outputs to deliver an impedance-compensated defibrillation shock through said switch to said patient based on a patient impedance; and, discharging said impedance-compensated defibrillation shock across said pair of electrode devices to said patient.

50. The method of claim 49, further comprising the step of monitoring the heart rate of said patient during said discharging step to determine if a subsequent defibrillation shock is necessary.

51. The method of claim 50, wherein if the subsequent defibrillation shock is needed, repeating said discharging step according to one of said voltage level outputs responsive to said patient impedance.

52. The method of claim 49, wherein the duration of said impedance-compensated defibrillation shock is controlled based on said patient impedance.

53. The method of claim 49, wherein said impedance-compensated defibrillation shock comprises one of monophasic, biphasic, and multiphasic.

54. The method of claim 49, wherein said discharging step is performed without removing body hair from said patient.

55. The method of claim 49, wherein the coupling of said pairs of electrode devices on said patient's body is performed without removing any clothing from said patient.

56. The method of claim 49, wherein the step or providing said energy storage device further comprises the step of providing a plurality of said capacitors and a plurality of resistors that are arranged in series, parallel, or a combination of series and parallel arrangement.

57. The method of claim 49, further providing an opening in said pair of electrode devices.

* * * * *